United States Patent
Mekideche

(10) Patent No.: US 7,604,806 B2
(45) Date of Patent: Oct. 20, 2009

(54) USE OF A LYOPHILISATE OF DEDIFFERENTIATED PLANT CELLS FOR SKIN DEPIGMENTATION AND/OR LIGHTENING

(75) Inventor: Nicole Mekideche, Ploubazlanec (FR)

(73) Assignee: Biotechmarine, Pontrieux (FR)

( * ) Notice: Subject to any disclaimer, the term of this patent is extended or adjusted under 35 U.S.C. 154(b) by 0 days.

(21) Appl. No.: 10/596,952

(22) PCT Filed: Dec. 3, 2004

(86) PCT No.: PCT/FR2004/003109

§ 371 (c)(1), (2), (4) Date: Jan. 16, 2007

(87) PCT Pub. No.: WO2005/072697

PCT Pub. Date: Aug. 11, 2005

(65) Prior Publication Data

US 2007/0098668 A1   May 3, 2007

(30) Foreign Application Priority Data

Dec. 29, 2003  (FR) ................... 03 15521

(51) Int. Cl.
*A61K 8/97* (2006.01)
(52) U.S. Cl. ................................. 424/195.17
(58) Field of Classification Search ....... None
See application file for complete search history.

(56) References Cited

U.S. PATENT DOCUMENTS

2003/0091659 A1 * 5/2003 Lu et al. ............ 424/727
2004/0115163 A1 * 6/2004 Gedouin et al. ............... 424/74
2005/0123499 A1 * 6/2005 Majmudar ................. 424/74
2007/0048243 A1 * 3/2007 Hansenne et al. ............. 424/74

FOREIGN PATENT DOCUMENTS

| EP | 1064932 A | | 1/2001 |
|---|---|---|---|
| FR | 2657011 | * | 7/1991 |
| FR | 2657011 A | | 7/1991 |
| FR | 2846242 A | | 4/2004 |
| JP | 05306213 A | * | 11/1993 |
| JP | 11180881 A | * | 7/1999 |
| JP | 11199464 A | * | 7/1999 |
| JP | 2003-160461 A | * | 6/2003 |
| KR | 2002-027834 | * | 4/2002 |
| WO | WO 01/82887 A | | 11/2001 |
| WO | WO 03/077881 | * | 9/2003 |
| WO | WO-03/077881 A | | 9/2003 |

OTHER PUBLICATIONS

NPS webpage, "Saltcedar," [retrieved from] http://www.nps.gov/plants/alien/fact/tama1.htm on Jan. 26, 2008.*
DeHaan et al., "Image-derived spectral endmembers as indicators of salinization," International Journal of Remote Sensing, Feb. 2003, vol. 24, No. 4, pp. 775-794 (Abstract only).*

* cited by examiner

Primary Examiner—Christopher R. Tate
(74) Attorney, Agent, or Firm—Birch, Stewart, Kolasch & Birch, LLP

(57) ABSTRACT

The invention relates to the use of at least one lyophilisate of dedifferentiated plant cells in a cosmetic or pharmaceutical composition for skin depigmentation and/or lightening purposes along with a protective regenerative effect. In addition, the invention relates to a topically-applied cosmetic or pharmaceutical composition comprising one such lyophilisate.

18 Claims, 4 Drawing Sheets

Negative Control

Positive Control (Kojic acid)

Cream PXTS + 0.1% AK205

Cream PXTS + 0.5% AK205

USE OF A LYOPHILISATE OF DEDIFFERENTIATED PLANT CELLS FOR SKIN DEPIGMENTATION AND/OR LIGHTENING

This application is the National Stage application of International Application No. PCT/FR 2004/003109 which was filed on Dec. 3, 2003, which claims priority to FR 0315521 filed in France on Dec. 29, 2003, the entire contents of which are hereby incorporated by reference.

The use of at least one lyophilisate of dedifferentiated plant cells in a cosmetic or pharmaceutical composition for skin depigmenting and/or lightening, for protecting and regenerating of the epidermis is disclosed.

The invention relates to the use of at least one lyophilisate of dedifferentiated plant cells in a cosmetic or pharmaceutical composition for depigmenting and/or lightening purposes of the epidermis along with a protective and regenerative effect. In addition, the subject-matter of the invention is a topically-applied cosmetic or pharmaceutical composition comprising at least one such lyophilisate.

The skin is a protecting envelope which constitutes the interface between the external environment and the internal organs. However, the skin is not hermetic and, as an absorbing organ, it allows the penetration of dissolved substances through pores and hair follicles.

The skin protects against cold, heat, radiations; against pressure, rubbing; against lesions caused by chemicals; against penetration of microorganisms, loss of water and of heat.

The natural protecting effect of the skin against ultraviolet light goes through a brown pigment, the melanin. Melanin is present in the basal cell layers of the epidermis: the melanocytes. It is synthesised from an amino acid, tyrosine, modified by an enzyme, tyrosinase. The synthesis of melanin is induced by UV light. The dark coloration of the skin is the first natural protection against the sun, which is very insufficient for very clear skins. The development of a tan is a consequence, due to the effect of the UV, of increased melanocyte activity in the melanin synthesis and of the storage of melanin in keratinocytes.

The amount of melanin and the number of melanocytes are genetically programmed factors which determine the colour of the skin.

An excessive and localised production of melanin gives rise to appearance of spots: freckles, chloasma, solar or senility lentigos, etc. Indeed, according to the most recent nomenclatures, aging spots are senility lentigos, and other spots are solar lentigos.

"Aging spots" are small, pale brown, flat, and generally round spots. They are found most frequently on the face, the back of the hands, the décolleté, and the forearms. They are caused by the combination of sun and aging. Their number increases with age. Under repeated action of UV light, melanocytes end up in an increased production of melanin.

Lentigines are brown "freckles" which don't disappear in winter, minuscule and numerous, very closely spaced one to another. They appear most often on the face, the shoulders, and the décolleté. They are due to an overdose of ultraviolet light and can be formed at a very early age.

"Chloasma" appear as big brown spots with uneven outlines, most often on the face, taking sometimes the shape of a mask. When these spots appear in the course of pregnancy, then we speak about chloasma, otherwise we speak about melasma. They are caused by hormonal stimulation (pregnancy, hormonotherapy) combined with an exposure to UV light.

All these types of spots can also be related to genetic inheritance and, therefore, to heredity.

Because of the ungainly aspect of this overconcentrated melanin, the availability of topical preparations, which prevent and/or subdue their appearance, is of utmost importance.

Manufacturers of cosmetic and pharmaceutical preparations are continuously looking for nonaggressive active ingredients to inhibit or to block directly or indirectly the synthesis of melanin, or to inhibit or to block the transfer of melanosoma to keratinocytes, and therefore to lighten these spots, while protecting these zones against solar pigmentation. Also manufacturers of cosmetic preparations are trying to find non-aggressive active ingredients for depigmenting in order to satisfy the growing desire of black or Asian populations to lighten the colour of their skin by offering a skin protecting product.

In order to overcome drawbacks of the other available tedious and/or aggressive depigmenting treatments (laser, cryotherapy), these active ingredients should at the same time protect the skin and/or stimulate the regeneration of the cells constituting the skin.

Indeed, skin protection and/or stimulation of the regeneration of skin cells at the same time continue to fight against a factor aggravating the spots: the skin aging due to multiple reasons.

The first reason for skin aging is "programmed" aging, which can be accelerated due to stress, to smoking addiction, arid to certain diseases. Over the years, the skin looses its elasticity, because the dermis produces less and less collagen and elastin fibres; hence the progressive weakening of the connective tissue and loosening of the skin. The renewal capacity of the epidermis also tends to be reduced, it becomes dryer and thinner because of its altered metabolism. Over time, the skin also experiences an ashiness, which results in a dull complexion and can be fought against by use of a lightening treatment, as well.

The second reason for aging is the reduction of hormonal production which results in a progressive diminution of the tissular, cellular, and organic functions. Hormones, such as growth hormone (HGH), testosterone, DHEA and melatonin, are produced in high amounts up to the age of 20 years and they favor cellular renewal.

These different reasons for aging in conjunction with environmental effects (various pollutions: exhaust gases, cigarette smoke, industrial smoke, chemical products, ... ) result in an excessive production of free radicals which are targeting different cell components: proteins, lipids, sugars and DNA, and which are a further reason of the skin aging. Driven by Some external influences, they are constantly searching other molecules in order to form a bond. Then they attack collagen fibres, cell membranes and the fatty layer of the skin. They modify the genetic inheritance of the cells, so that the quality of the new skin cells diminishes.

The body protects itself against these aggressors by different enzymatic systems opposing these oxidation reactions (anti-oxidants). But from the age of 20 years, the natural defence mechanisms undergo a progressive weakening, in a way that the skin alone is not able to defend itself any more.

The Applicant has discovered in a surprising and unforeseen way that a lyophilisate of dedifferentiated plant cells allows to achieve this combination of desired effects: the depigmenting and/or lightening of the epidermis with a total innocuousness, while the epidermis is being protected and regenerated.

The dedifferentiated cells maintain all cellular potentialities as stem cells. They express all the genes of their genome, and therefore all the proteins which enable each type of specialized cells to protect itself against the external environment.

In particular, preference is given to the use of dedifferentiated plant cells of a halophile plant, such as the species Salicornia ramossisima (Salicorne), Sueda vera, Beta maritima, obione portulacoides, Armeria maritima, Crithmum maritimum (Criste Marine), Ophrys sphegodes, Artemia vulgaris, Muscaris comosum, Eryngium maritimum, Sanguisorba minor, Cochlearia officinalis, Fumaria officinalis, Vincetoxicum fullonum, Dipsacus fullonum, Heracleum spondylium, hula critbmoides, Inula brittanica, Inula viscosa, most particularly the dedifferentiated plant cells of Criste Marine (Crithmum maritimum). The halophile plants, also called halophytes, are plants which tolerate high salinity soils. They have developed defence systems against the aggressive external medium which they are colonizing. In particular, the halophytes are seaside plants capable to stand a high salinity soil, humidity and wind. They are permanently fighting to maintain the osmotic pressure in their cells, the water tending to cross the plasmic membrane towards the extracellular compartment with higher sodium content.

Thus, the first aspect of the invention is the use of at least one lyophilisate of dedifferentiated plant cells in or for the manufacturing of a cosmetic or pharmaceutical composition, the said lyophilisate allowing to depigment and/or to lighten, to protect and to regenerate the epidermis.

"Dedifferentiated plant cell" means any plant cell which does not present characteristics of specialization and which can, itself, regenerate a whole young plant of the plant from which it is derived. This cell can be isolated from any sample of a whole plant or organ of plant, such as leaves, stems, roots, seeds, flowers, petals, anthers, fruits, etc., called explant.

Preferably, use is made of a fragment of leaf or of a seed as explant.

A very particular preference is given to the culture in vitro of the explant. By "culture in vitro" is meant the whole of techniques of the prior art known by those skilled in the art, which allow, under perfectly controlled conditions, to regenerate an organ or a whole plant from an explant cultured in or on a defined nutrient medium. These perfectly controlled conditions allow to obtain a perfect reproducibility and homogeneity of young plants. In particular, this method of culture provides for ad infinitum identical clones. Among the in vitro culture methods and media described in the prior art, the media of Gamborg (1968), of Murashige and Skoog (1962), of Morel (1970), etc., the formulation of which is described in "Plant Culture Media: formulations and uses" by E. F. George, D J M Puttock and H. J. George (Exegetics Ltd 1987), can be mentioned as examples.

In biological systems, molecular oxygen is stable and has a low reactivity. It behaves as an electron acceptor and its reduction ends up in the production of water. But the incomplete reduction of $O_2$ induces the production of free radicals and of metabolites such as the superoxyde anion $O_2^-$, the toxic perhydroxyde radical $HO_2^-$ (in the presence of ferrous iron, the reaction can result in highly aggressive OH), or hydrogen peroxyde $H_2O_2$.

When a halophile plant is used, it is particularly important to develop an in vitro cell culture which provides for biomass ad infinitum and reproducible in order to protect these species, the halophytes being in danger of sea pollution.

In a particular embodiment of the invention, it is also possible to modify certain culturing conditions (pH, temperature, ambient gaseous composition, culture medium composition, luminosity). The dedifferentiated cells tend then to produce more or less of certain intracellular substances.

The second aspect of the invention is a topically-applied cosmetic or pharmaceutical composition wherein the composition comprises, in a physiologically acceptable base, from of 0.05 to 2%, preferably from of 0.1 to 1%, most preferably from of 0.5%, of at least one lyophilisate as described hereabove.

Indeed, such a lyophilisate can be used as the only active ingredient of the composition according to the invention. However, several lyophilisates can be added to the base of the composition of the invention.

In a first particular embodiment of the invention, at least one lyophilisate of dedifferentiated plant cells is used for the manufacturing of a cosmetic or pharmaceutical composition expected to rejuvenate the skin aspect.

In a second particular embodiment of the invention, at least one lyophilisate of dedifferentiated plant cells is used for the manufacturing of a cosmetic or pharmaceutical composition expected to treat spots called lentigos.

In a third particular embodiment of the invention, at least one lyophilisate of dedifferentiated plant cells is used for manufacturing of a cosmetic or pharmaceutical composition expected to lighten black or asian skins.

The following Examples illustrate the invention without limiting its scope.

EXAMPLE 1

Figure 1:
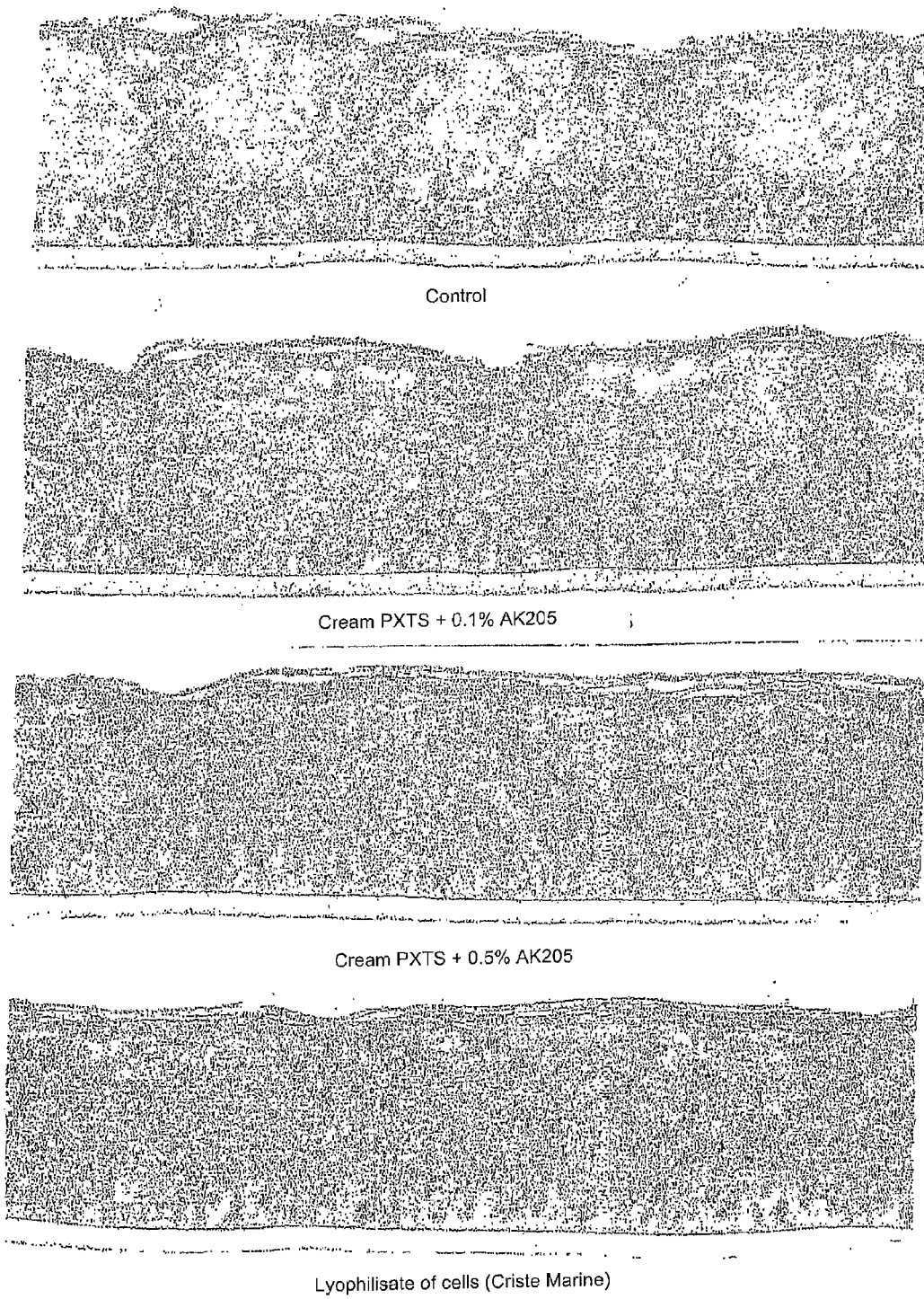
FIG. 1: general morphology, staining with hematoxylin/eosin (HES) on simple reconstructed epidermis SKINETHIC® (keratinocytes)

In Vitro Culture of Dedifferentiated Criste Marine Cells from a Plant Tissue

1—Obtaining of Primary Callus

Pieces of tissue in the selected zone (minimum 3 cm) stem, leaves . . . , are cut out using a pair of scissors. From this stage of manipulation, all operations have to be carried out in sterile atmosphere in a laminar flow hood.

For sterilizing the plant material, the tissues are immerged for 30 s in ethanol, then the solvent is eliminated, the tissues are rinsed with 3×100 ml of sterile $H_2O$, immerged for 15 min in sodium hypochlorite with addition of a few drops of Tween 20 and rinsed with 3×100 ml sterile $H_2O$.

For tissue culturing, the tissue fragments are put into a sterile Petri dish (125 mm), the tissue fragments are cut (2 to 3 mm), taking care to remove the parts bleached with sodium hypochlorite. The thus obtained explants are slightly incised et plated out half-buried in the agar nutrient medium (Table 1).

2—Callus Replanting

At this stage of manipulation, all operations have to be carried out in sterile atmosphere in a laminar flow hood under. 2 to 3 cell clusters (1 to 2 cm) are taken at the callus level with a spatula.

These clusters are plated out and distributed on the fresh medium.

TABLE 1

COMPOSITION OF THE SOLID CULTURE MEDIUM

|  | mg/l |
|---|---|
| Macroelements | |
| $KNO_3$ | 2500 |
| $(NH_4)_2SO_4$ | 134 |
| $CaCl_2, 2H_2O$ | 150 |
| $NaH_2PO_4, 2H_2O$ | 300 |
| $MgSO_4, 7H_2O$ | 250 |
| Microelements | |
| $MnSO_4, H_2O$ | 16.9 |
| $ZnSO_4, 7H_2O$ | 8.6 |
| $H_3BO_3$ | 6.2 |
| KI | 0.83 |
| $Na_2MoO_4, 2H_2O$ | 0.25 |
| $CuSO_4, 5H_2O$ | 0.025 |
| $FeSO_4, 7H_2O$ | 27.8 |
| Vitamins | |
| myo-inositol | 100 |
| nicotinic acid | 1 |
| calcium-D(+)-panthotenate | 1 |
| (+)-biotine | 0.01 |
| pyridoxal chlorhydrate | 1 |
| thiamine dichloride | 1 |

| Organic compounds | g/l |
|---|---|
| saccharose | 30 |

| Phytohormones | mg/l |
|---|---|
| naphtalene acetic acid | 1.5 |
| 2,4 dichlorophenoxyacetic acid | 0.5 |
| kinetine | 0.5 |

| Gelling agent | g/l |
|---|---|
| agar | 9 |

3—Expansion of Callus Cells in Liquid Medium

Maintenance Seed:

The callus cells are transferred into a liquid medium identical to the solid agar-free medium (Table 1). They are grown under agitation (110 rpm/min), at 25° C., in continuous white light (3500 lux, fluorescent tubes "daylight") in 250 mL Erlenmeyer flasks, at a rate of 50 mL per Erlenmeyer flask.

They are diluted every 10-11 days to a 1:4 split, i.e. 100 mL in 400 mL.

Production of Dry Material

The cells are grown from a dilution to 1:4 split of the maintenance seed in Erlenmeyer flasks of 5L, at a rate of 2L of culture per Erlenmeyer flask, under agitation (110 rpm/min), at 25° C. in continuous white light (3500 lux, fluorescent tubes "daylight") and this for 12 to 13 days.

It should be noted, that the 2,4-dichloro-phenoxyacetic acid is completely metabolised and will not be found in the final product.

EXAMPLE 2

Preparation of a Lyophilisate of Dedifferentiated Criste Marine Cells

The liquid cell culture in suspension is subjected to centrifugation in order to pellet the cells.

The cells are passed through a sieve of 150-200 μm, frozen, then lyophilised in a plate lyophiliser.

EXAMPLE 3

Demonstration on Reconstructed Epidermis Skinethic®Of the Absence of Toxicity of a Cosmetic Preparation Containing a Lyophilisate of Dedifferentiated Criste Marine Cells The reconstructed epidermis SKINETHIC® is a human epidermis model developed and marketed by SkinEthic Laboratories Company (Nice, France).

1—On Reconstructed Simple Epidermis SKINETHIC® (Constituted Only of Keratinocytes):

Keratinocytes of human origin are seeded onto polycarbonate filters of 0.63 $cm^2$ in a defined (modified MCDB 153) and supplemented medium. The cells are grown for 14 days at the air/liquid interface, the growth medium is being changed every two days.

The thus formed epidermis were used for carrying out the study beginning with the 17th day of culture.

A preliminary test was carried out in order to determine the contact time and the cytotoxicity non-inducing amount of the product applied to the reconstructed epidermis.

All tests were carried out in duplicate with

Batch 1: control epidermes not receiving any product

Batch 2 treated epidermes receiving the cream PXTS+0.1% AK205

Batch 3: treated epidermes receiving the cream PXTS+0.5% AK205

Batch 4 treated epidermes receiving the product cell lyophilisate (AK 205)

AK205=lyophilisate of dedifferentiated Criste Marine cells obtained in Examples 1 and 2.

PXTS=for very dry skins

Epidermes fixed in a 10% formaldehyde solution were embedded into paraffin blocs. The vertical sections of 4 microns were stained with hematoxylin/eosin and photographed through an optical microscope.

The cultures should present basal, spinous, granular and intact cornea cellular layers, showing orthokeratosis, and the epidermal stratification should be regular and normal. The cells of the basal layer should be vertically polarized. Numerous keratohyaline grains should be visible (violet) in the granular layer just under the cornea layer.

The products, cream PXTS+0.1% AK205, cream PXTS+ 0.5% AK205 and the product lyophilisate of Criste Marine cells (AK 205), applied at a rate of 2 μL per $cm^2$ onto reconstructed epidermes treated for 24 hours, did not induce any toxicity as compared to control epidermes. The histological images of treated epidermes, after staining with hematoxylin/eosin, are comparable to those of control epidermes (see FIG. 1).

2—On Reconstructed Epidermis SKINETHIC® Including Melanocytes

Keratinocytes of human origin and melanocytes are seeded onto polycarbonate filters of 0.63 $cm^2$ in a defined (modified MCDB 153) and supplemented medium. The cells are grown for 10 days on the air/liquid interface, the growth medium is being changed daily.

The thus formed type IV epidermes (=negroid) were used from the 10th day of culture.

A preliminary test was carried out in order to determine the contact time and the cytotoxicity non-inducing amount of the product applied onto reconstructed epidermis.

The test was carried out in duplicate with
Batch 1: control epidermes not receiving any product
Batch 2: positive control epidermes receiving 2% kojic acid
Batch 3: treated epideimes receiving the cream PXTS+0.1% AK205
Batch 4: treated epidermis receiving the cream PXTS+0.5% AK205
AK205=lyophilisate of dedifferentiated Criste Marine cells obtained in Examples 1 and 2.

The epidermes fixed in a 10% formaldehyde solution were embedded in paraffin blocs. The vertical sections of 4 microns were stained with hematoxylin/eosin and photographed through an optical microscope.

The cultures should show basal, spinous, granular and intact cornea cellular layers, showing orthokeratosis, and the epidermal stratification of should be regular and normal. The basal layer cells should be vertically polarized. A great number of keratohyaline grains should be visible (violet) in the granular layer just under the cornea layer.

Figure 2:
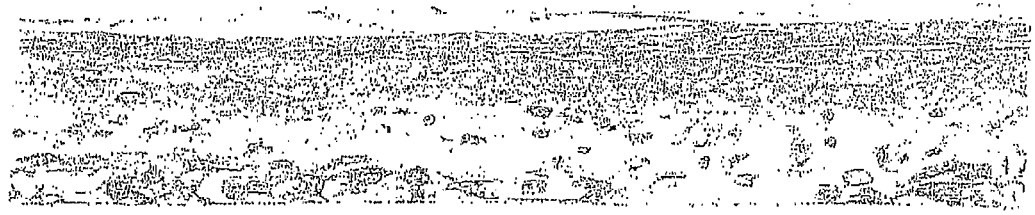
FIG. 2: general morphology, staining with hematoxylin/eosin (HES) on simple reconstructed epidermis SKINETHIC® comprising melanocytes
Figure 2:
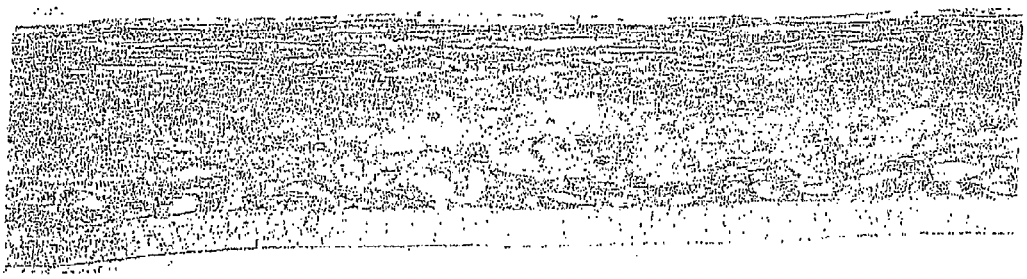
Figure 2:
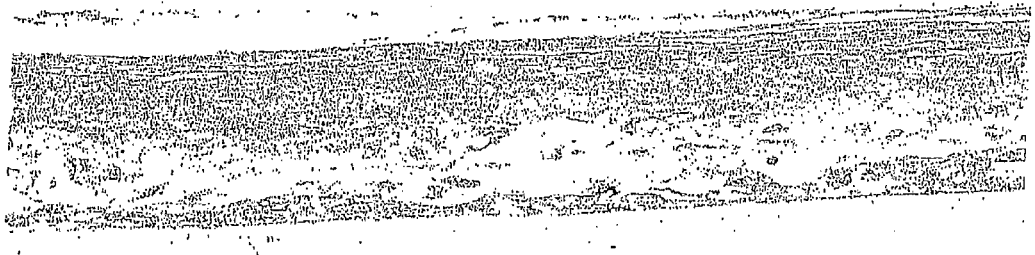
Figure 2:

The products cream PXTS+0.1% AK205 and cream PXTS+0.5% AK205 applied at a rate of 2 μL per cm$^2$ onto the reconstructed epidermes treated for 24 hours, did not induce any toxicity as compared to control epidermes. The histological images of treated epidermes, after staining with hematoxylin/eosin, are comparables to those of control epidermes (see FIG. 2).

EXAMPLE 4

Assessment on Reconstructed Epidermes Skinethic® of The Depigmenting Effect of a Cosmetic Preparation Containing a Lyophilisate of Dedifferentiated Criste Marine Cells Including Melanocytes 1- Experimental Protocol Keratinocytes of human origin and melanocytes are seeded onto polycarbonate filters of 0.63 cm$^2$ in a defined (modified MCDB 153) and supplemented medium. The cells are grown for 10 days at the air/liquid interface, the growth medium is being changed daily.

The thus formed type IV epidermis (=negroid) were used from the 10th day of culture.

All tests were carried out in duplicate with
Batch 1 control epidermes not receiving any product
Batch 2: positive control epidermes receiving 2% kojic acid
Batch 3: treated epidermes receiving the cream PXTS+0.1% AK205
Batch 4: treated epidermes receiving the cream PXTS+0.5% AK205
AK205 lyophilisate of dedifferentiated Criste Marine cells obtained in Examples 1 and 2.

The assessment of the synthesis of intracellular melanin (qualitative study) was carried out by spectrometry at 475 nm after that the cells were suspended, then dissolved in NaOH (1N) and dimethyl sulfoxide for 30 minutes.

At the end of the incubation period, the culture medium was withdrawn, the epidermes were rinsed with PBS (Phosphate Buffer Saline) and contacted with 1% Triton X-100 (Sigma, France), then incubated for 10 minutes. The enzyme reaction was induced by addition of 10 mM $Ca^{2+}$- and de $Mg^{2+}$-free L-Dopamine (Sigma, France) in PBS.

After incubation for 1 hour at 37° C. in darkness, the tyrosinase activity was assessed by measurement of the absorption at 475 nm by means of a spectrophotometer.

2- Results a) Assay of the Melanin

The obtained results are resumed in the following Table:

|  | Absorbance (475 nm) | % |
| --- | --- | --- |
| Negative control | 0.160 ± 0.02 | — |
| Positive control | 0.09 ± 0.01 | −44 |
| Cream PXTS + 0.1% AK205 | 0.139 ± 0.02 | −13 |
| Cream PXTS + 0.5% AK205 | 0.101 ± 0.01 | −37 |

The obtained results show that the cream PXTS+0.5% AK205 induced a significant diminution of the rate of melanin at the level of the reconstructed epidermes integrating melanocytes (−37%). The cream PXTS+0.1% AK205 reduced slightly this rate (−13%) as compared to the positive control 2% kojic acid (−44%).

b) Assessment of Tyrosinase Activity

The obtained results are resumed in the following Table

|  | Absorbance (475 nm) | % |
| --- | --- | --- |
| Negative control | 0.245 ± 0.03 | — |
| Positive control | 0.153 ± 0.01 | −38 |
| Cream PXTS + 0.1% AK205 | 0.198 ± 0.02 | −19 |
| Cream PXTS + 0.5% AK205 | 0.167 ± 0.02 | −32 |

The obtained results reveal that the product cream PXTS+ 0.5% AK205 induced a significant diminution of the tyrosinase activity at the level of the reconstructed epidermes with integrated melanocytes (−32%) as compared to the positive control (−38%). A slight diminution (−19%) was observed after treatment with the product cream PXTS+0.1% AK205.

In conclusion, under the applied experimental conditions, the product cream PXTS+0.5% AK205 showed a net depigmenting activity on the reconstructed epidermes integrating melanocytes. A more limited but real activity was observed with the cream PXTS+0.1% AK205.

EXAMPLE 5

Detection on Reconstructed Epidermis Skinethic® of The Anti-Radical Effect of a Cosmetic Preparation Containing a Lyophilisate of Dedifferentiated Criste Marine Cells 1- Why to Assay the Malondialdehyde?

In biological systems, the molecular oxygen is stable and has a low reactivity. It behaves as an electron acceptor and its reduction ends up in the production of water. But the incomplete reduction of $O_2$ induces the production of free radicals and of metabolites such as the superoxyde anion $O_2^-$, the toxic perhydroxyde radical $HO_2^-$ (in the presence of ferrous iron, the reaction can result in highly aggressive $OH^-$), or the hydrogen peroxyde $H_2O_2$.

The superoxyde dismutase (SOD) protects the membranes by a very quick dismutation of $O_2^-$ in $H_2O_2$. The relatively stable $H_2O_2$ is reduced to water ($H_2O$) by the catalase and the peroxydase. These free radicals, resulting from the incomplete reduction of $O_2$, are sensitive at the level of double bonds, which favour the appearance of other free radicals by electronic delocalisation. The initiation of the radical chain reaction occurs at the level of polyinsaturated fatty acids. The chain reaction is then triggered inside the cell membrane causing the release of malondialdehyde (MDA) and other aldehydes and alkanes as well, which are products of decomposition. These can be determined by reaction with thiobarbituric acid (TBA).

The assay of the MDA, which is one of the essential cytotoxicity markers due to oxidative processes and to stress, provides for an indicator informing on the antiradical activity of a given substance is made available.

2- Experimental Protocol

Keratinocytes of human origin are seeded onto polycarbonate filters of 0.63 cm$^2$ in a defined (modified MCDB 153) and supplemented medium. The cells are grown for 14 days at the air/liquid interface. The culture medium is being changed every two days.

The thus formed epidermes were used for the carrying out the study from the 17th day of culture.

The assay was performed in triplicate after a 24 hours of contact time of the product with the epidermes:

Batch 1: negative control epidermes not receiving any product

Batch 2: treated epidermes receiving the product cream PXTS+0.1% AK205

Batch 3: treated epidermes receiving the product cream PXTS+0.5% AK205

Batch 4: treated epidermes receiving the product cell lyophilisate (Criste Marine)

The examined products were applied onto the surface of each treated epidermis with a rate of 2 μL/cm$^2$.

=>Malondialdehyde Extraction

After a 24 hours contact time of the product with the epidermes, these were suspended in:

250 μL of Tris 50 mM buffer, pH 8, containing 0.1M NaCl; 20 mM EDTA
    25 μL of 7% SDS
    300 μL HCl (0.1 N)
    38 μL 1% phosphotungstic acid in water
    300 μL 0.67% thiobarbituric acid in water After incubation for 1 hour at 50° C. in darkness and cooling in ice-water, 300 ml of n-butanol were added to each tube. These were subjected to centrifugation at 10 000 g, at 0° C., for 10 min. The supernatant was recovered for assaying the MDA.

=>Malondialdehyde Assay

The MDA was assayed by measuring of the fluorescence after separation of the complex MDA-TBA by HPLC (High-Pressure Liquid Chromatography).

Pump Bischoff Model 2.200
    Automatic injector Alcoot Model 788 autosampler
    Ultrasep CIS Column (30 cm×0.18 cm) porosity 6 mm
    Detector of fluorescence, jasco 821-FI The detection of the fluorescence was carried out with an excitation at 515 nm and an emission at 553 nm. The used eluent comprises methanol:water, 40:60 (v/v), the pH of which was adjusted with KOH 1M.

The quantification was carried out in relation to standards treated as the samples (0.125; 0.25; 0.5 and 1 mM) using a computer programme ICS (Pic 3) (Instrumentation, Consumable, Service).

=>Assay of Proteins

The assay of proteins was carried out following the method of BRADFORD. The increase in the absorbance at 595 nm is proportional to the concentration of proteins determined by a spectrophotometer UNI CAM 8625.

3—Results a) Physiological Lipoperoxidation

The obtained results are resumed in the following Table

|  | MDA (μM/mg proteins) | % |
|---|---|---|
| Control | 652 ± 31 | — |
| Cream PXTS + 0.1% AK205 | 638 ± 47 | −2 (ns) |
| Cream PXTS + 0.5% AK205 | 620 ± 32 | −5 (ns) |
| Cell lyophilisate | 594 ± 57 | −9 (ns) | ns: not significant ns: not significant

The results show that the examined products do not induce any MDA release under the physiological conditions, as compared to the untreated control.

b) Lipoperoxidation Induced by UVB

The obtained results are resumed in the following Table

|  | MDA (μM/mg proteins) | % |
|---|---|---|
| Control | 652 ± 31 | — |
| UVB (150 mJ/cm$^2$) | 832 ± 63 | +28* |
| Cream PXTS + 0.1% AK205 + UVB (150 mJ/cm$^2$) | 660 ± 51 | −21** |
| Cream PXTS + 0.5% AK205 + UVB (150 mJ/cm$^2$) | 625 ± 42 | −25** |
| Cell lyophilisate + UVB (150 mJ/cm$^2$) | 602 ± 37 | −28** |

*compared to negative control
**compared to positive control irradiated with UVB The obtained results have shown a significant protection provided by the products, cream PXTS+0.1% AK205, cream PXTS+0.5% AK205 and cell lyophilisate (Criste Marine), applied onto the surface of the reconstructed epidermis SKINETHIC®, against the lipoperoxidation induced by ultraviolet B light (150 mj/cm$^2$)

The percentage of reduction of the MDA production is respectively of −21, −25 and −28% for the cream PXTS+0.1% AK205, the cream PXTS+0.5% AK205 and the product cell lyophilisate (Criste Marine) as compared to the irradiated epidermes.

The irradiation with UVB (positive control) induced an increase of +28% of the MDA production, the application of the products cream PXTS+0.1% AK205, cream PXTS+0.5% AK205 and the product cell lyophilisate (Criste Marine) prior to the exposure allowed to maintain the MDA production at its physiological level.

EXAMPLE 6

Determination on Reconstructed Epidermis Skinethic®Of the Stimulating Effect of a Cosmetic Preparation Containing a Lyophilisate of Dedifferentiated Criste Marine Cell 1—Assessment Criteria of the Stimulation The cell culture of human keratinocytes allowed to describe in more details the specific effects of vitamin A derivatives on markers of the gradual differentiation of epidermis: the expression of KI-67 in the supra-basal layer is stimulated, the expression of keratines typical for epidermal hyperproliferation (K19, K13) is induced, a loss of polarity in the basal cells layer is observed, whereas the synthesis of filaggrine, the protein responsible for the packaging of keratins in the stratum corneum, is inhibited. The grains of keratohyaline, located in the granular layer, and with a high content of filaggrine, disappear within 24h in the presence of retinoic acid, 0.05% (vitamin A acid) in the culture medium. The retinoids therefore induce an overall stimulation of the proliferation and an inhibition of the epidermal differentiations (Rosdy, M. and al., In Vitro Toxicology, Vol. 10 no.1, p. 39-47, 1997, "Retinoic acid inhibits epidermal differentiation when applied topically on the stratum corneum of epidermis formed in vitro by human keratinocytes grown on defined medium")

The filaggrine and the protein KI-67 can L therefore be used as markers of the epidermal differentiation.

2—Epidermal Differentiation Study:

Protocol

Keratinocytes of human origin are seeded onto polycarbonate filters of 0.63 cm$^2$ in a defined (modified MCDB 153) and supplemented medium. The cells are grown for 14 days at the air/liquid interface. The culture medium is being changed every two days.

The thus formed epidermis were used for carrying out the study from the 17th day of culture.

The assay was carried out in triplicate after 24 hours of contact time of the products with the epidermis Batch 1: negative control epidermes not receiving any product Batch 2: treated epidermes receiving the product cream PXTS+0.1% AK205

Batch 3 treated epidermes receiving the product cream PXTS+0.5% AK205

Batch 4 treated epidermes receiving the product cell lyophilisate (Criste Marine)

The control epidermes not receiving any product and the treated epidermes receiving the studied products during 24 hours of contact time were frozen at −80° C. After embedding in paraffin blocs, these epidermes were cut, then treated by immuno-histochemistry.

This reaction was carried out with a filaggrine recombinant monoclonal antibody.

Results: Inhibition of the Differentiation of Epidermal Cells

Figure 3:
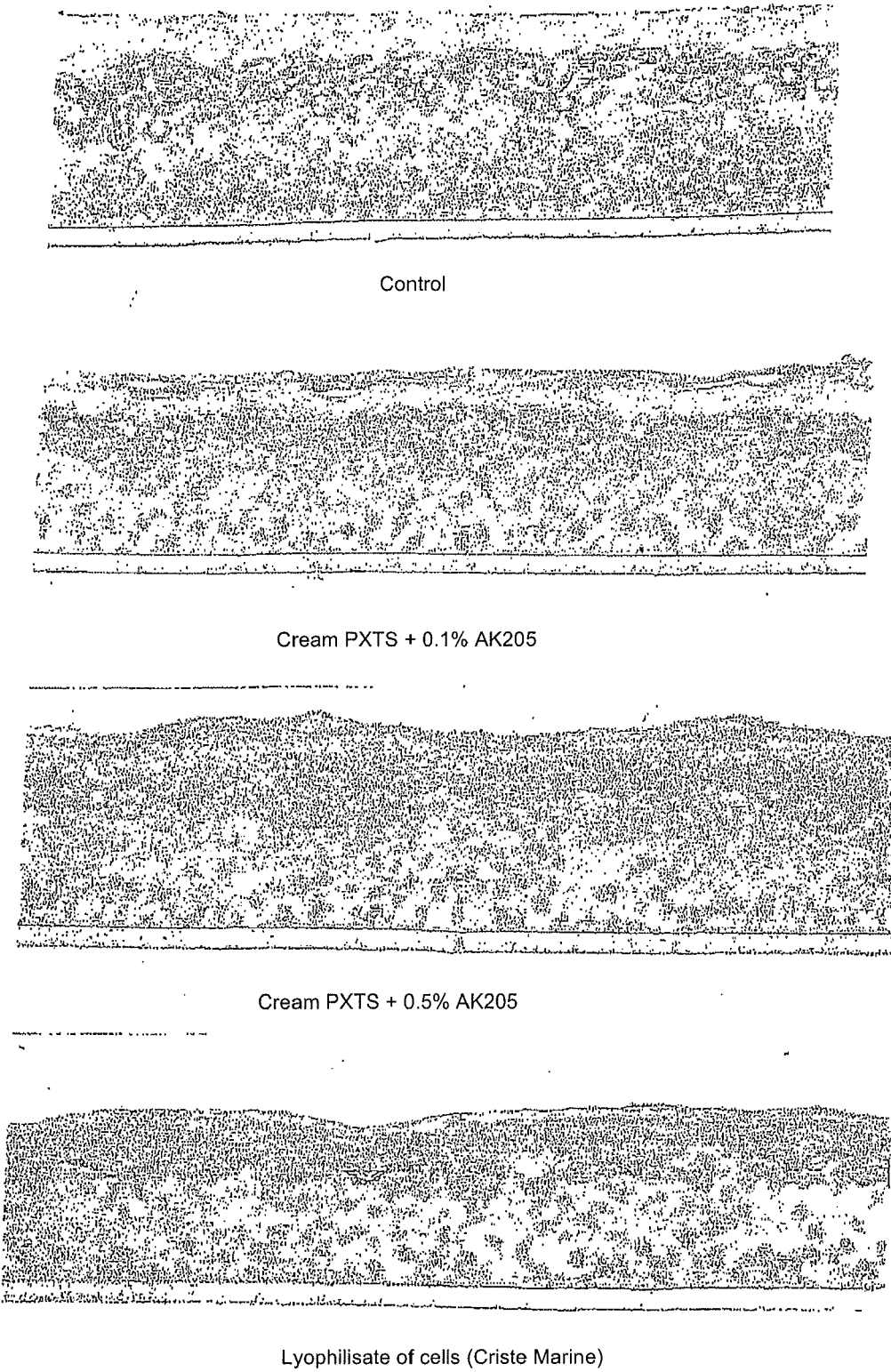
FIG. 3: labelling of the filaggrine

The comparative observation of reconstructed control epidermes and epidermes treated with the products cream PXTS+0.1% AK205, cream PXTS+0.5% AK205 and cell lyophilisate (Criste Marine), revealed a difference in the labelling density of the filaggrine at the level of the granular layer (see FIG. 3).

Indeed, under the physiological conditions, the epidermes treatment with:
  cream PXTS+0.1% AK205: induced a net diminution of the epidermal differentiation shown in the net reduction of the labelling of filaggrine compared to the not treated controls,
  cream PXTS+0.5% AK205: induced a net diminution of the epidermal differentiation shown in the net reduction of the labelling of filaggrine compared to the not treated controls,
  cell lyophilisate (Criste Marine) induced a net diminution of the epidermal differentiation which was shown in the net reduction of the labelling of filaggrine compared to the not treated control.

3 Study of the Proliferative Activity of the Cells of Epidermal Basal Cells Layer Protocol Keratinocytes of human origin are seeded onto polycarbonate filters of 0.63 cm$^2$ in a defined (modified MCDB 153) and supplemented medium. The cells are grown for 14 days at the air/liquid interface. The culture medium is being changed every two days.

The thus formed epidermes were used for carrying out the study from the 17th day of culture.

The activity of the products was revealed by immunohistochemical labelling.

The assay was carried out in triplicate after 24 hours of contact time of the products with the epidermes Batch 1: negative control epidermes not receiving any product L Batch 2: treated epidermes receiving the product cream PXTS+0.1% AK205

Batch 3: treated epidermes receiving the product cream PXTS+0.5% AK205

Batch 4: treated epidermes receiving the product cell lyophilisate (Criste Marine)

The control epidermes not receiving any product and the treated epidermes receiving the examined products for 24 hours contact time, were fixed in 10% formaldehyde. After embedding in paraffin blocs, these epidermis were cut and treated by immuno-histochemistry.

This reaction was carried out with the antibody MIB1 (Immunotech), a recombinant peptide of the nuclear antigen KI-67.

The revealing was carried out by the peroxidase-antiperoxidase method after antigenic demasking by heat pretreatment.

The labelling with the chromogen DAB reveals in brown colour the nuclear sites KI-67 of the growing cell fraction expressed in phases
=>G1 and S=latency and cell synthesis phases
=>G2=dedoubling phase of the cell constituents
=>M=mitosis The mitotic index was assessed as 6 by counting the coloured nuclear sites, at the rate of 10 fields per slide through an optical microscope, magnification×250, compared to control epidermis slides.

Results: stimulation of the epidermal cell proliferation.

The results are resumed in the following Table

|  | Mean value of coloured nuclei per count field through microscope |
|---|---|
| Control | 7 ± 2 |
| Cream PXTS + 0.1% AK205 | 8 ± 2 |
| Cream PXTS + 0.5% AK205 | 12 ± 2 |
| Cell lyophilisate | 14 ± 3 |

Figure 4:
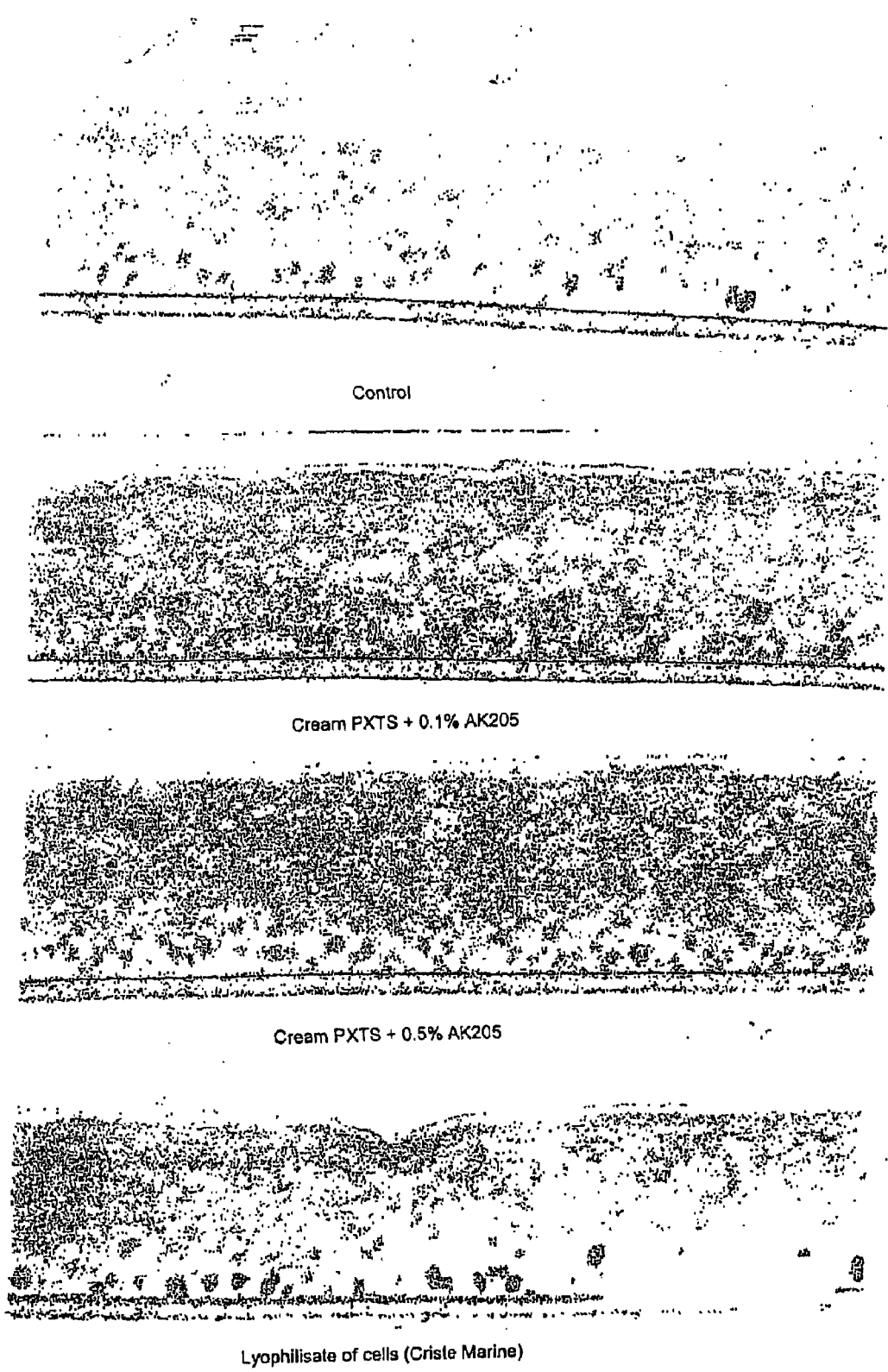
FIG. 4: labelling of KI-67 (evaluation of the mitotic index)

The count of the brown coloured nuclei sites of all samples, after immunhistochemical treatment, revealed that the product:
  cream PXTS+0.1% AK205: induced a slight but significant increase of the basal layer cells multiplication. The number of the coloured nuclei sites is comparable to that of the not treated controls (see FIG. 4).
  cream PXTS+0.5% AK205: induced a slight but significant increase of the basal layer cells multiplication as compared to the not treated control. The number of coloured nuclei sites is higher than that of the not treated controls (see FIG. 4).

cell lyophilisate (Criste Marine): induced a significant increase of the basal layer cell multiplication as compared to the not treated control. The number of the coloured nuclei sites is much more higher than that of the not treated controls (see FIG. 4).

The invention claimed is:

1. A topically applied cosmetic or pharmaceutical composition for depigmenting or lightening the epidermis with a protective and regenerating effect, comprising one lyophilisate of dedifferentiated plant cells in a physiologically acceptable base, wherein said dedifferentiated plant cells are Criste marine (Crithmum maritimum) cells.

2. The topically-applied cosmetic or pharmaceutical composition according to claim 1, wherein the composition comprises from 0.05% to 2% of the lyophilisate.

3. The topically-applied cosmetic or pharmaceutical composition according to claim 1, wherein the composition comprises from 0.1% to 1% of the lyophilisate.

4. The topically-applied cosmetic or pharmaceutical composition according to claim 1, wherein the composition comprises 0.5% of the lyophilisate.

5. The composition according to any one of claims 1 to 4, wherein said composition rejuvenates the skin.

6. The composition according to any one of claims 1 to 4, wherein said composition treats pigment spots.

7. The composition according to any one of claims 1 to 4, wherein said composition lightens black or asian skin.

8. The composition according to claim 1, wherein the dedifferentiated plant cells are obtained by in vitro culture.

9. The composition according to claim 8, wherein the dedifferentiated plant cells obtained by in vitro culture are cell lines.

10. The composition according to claim 1, wherein the lyophilisate blocks tyrosinase activity.

11. The composition according to claim 1, wherein the lyophilisate has an anti-radical effect.

12. The composition according to claim 1, wherein the lyophilisate stimulates the proliferation of epidermal basal layer cells.

13. The composition according to claim 1, wherein the lyophilisate inhibits epidermal differentiation.

14. A method for depigmenting or lightening the epidermis with a protective and regenerative effect comprising topically applying an effective amount of the composition according to claim 1 to said epidermis.

15. The method according to claim 14, wherein the composition depigments or lightens the epidermis by blocking the tyrosinase activity.

16. The method according to claim 14, wherein the composition protects the epidermis by an anti-radical effect.

17. The method according to claim 14, wherein the composition regenerates the epidermis by a stimulating effect on the proliferation of the cells of the epidermal basal layer.

18. The method according to claim 14, wherein the composition regenerates the epidermis by an inhibitory effect on the epidermal differentiation.

* * * * *